(12) United States Patent
Rose

(10) Patent No.: US 11,382,871 B2
(45) Date of Patent: Jul. 12, 2022

(54) PHARMACEUTICAL COMPOSITION CONTAINING CURCUMIN

(71) Applicant: BRIU GmbH, Koenigstein (DE)

(72) Inventor: Uwe-Bernd Rose, Koenigstein (DE)

(73) Assignee: BRIU GMBH, Koenigstein (DE)

( * ) Notice: Subject to any disclaimer, the term of this patent is extended or adjusted under 35 U.S.C. 154(b) by 1249 days.

(21) Appl. No.: 14/437,722

(22) PCT Filed: Jul. 24, 2013

(86) PCT No.: PCT/EP2013/065661
§ 371 (c)(1),
(2) Date: Aug. 4, 2015

(87) PCT Pub. No.: WO2014/063844
PCT Pub. Date: May 1, 2014

(65) Prior Publication Data
US 2015/0342904 A1 Dec. 3, 2015

(30) Foreign Application Priority Data

Oct. 22, 2012 (DE) ...................... 10 2012 219 219.0

(51) Int. Cl.
| | | |
|---|---|---|
| *A61K 31/12* | (2006.01) | |
| *A61K 47/22* | (2006.01) | |
| *A61K 47/10* | (2017.01) | |
| *A61K 47/12* | (2006.01) | |
| *A61K 9/00* | (2006.01) | |

(52) U.S. Cl.
CPC ............ *A61K 31/12* (2013.01); *A61K 9/0019* (2013.01); *A61K 47/10* (2013.01); *A61K 47/12* (2013.01); *A61K 47/22* (2013.01)

(58) Field of Classification Search
CPC ................................................ A61K 36/9066
USPC ....................................................... 424/756
See application file for complete search history.

(56) References Cited

U.S. PATENT DOCUMENTS

| | | | | |
|---|---|---|---|---|
| 2010/0197584 A1* | 8/2010 | Banerjee | ............ | A61K 36/9066 514/1.1 |
| 2011/0038965 A1* | 2/2011 | McKay | .................. | A61K 31/14 424/742 |

FOREIGN PATENT DOCUMENTS

| | | | | | |
|---|---|---|---|---|---|
| CN | 101138550 A | | 3/2008 | | |
| CN | 101548946 A | * | 10/2009 | | |
| CN | 102225048 A | * | 10/2011 | ............... | A61P 3/06 |
| CN | 101548946 B | * | 4/2012 | | |
| CN | 101548946 B | | 4/2012 | | |
| CN | 102670574 A | * | 9/2012 | | |
| EP | 2 228 062 A1 | | 9/2010 | | |
| WO | WO 2009/061152 A2 | | 5/2009 | | |
| WO | WO-2009061152 A2 | * | 5/2009 | ............ | A61K 31/12 |
| WO | WO 2010/010431 A1 | | 1/2010 | | |
| WO | WO 2011/101859 A1 | | 8/2011 | | |
| WO | WO 2012/035480 A2 | | 3/2012 | | |
| WO | WO-2012035480 A2 | * | 3/2012 | ............. | A61P 25/28 |

OTHER PUBLICATIONS

Joshi et al. "A Comparative Study: Solution Stability and Dissolution Behavior of Solid Dispersions Curcumin", Indian Journal of Novel Drug Delivery, 2(3), Jul.-Sep. 2010, 88-95. (Year: 2010).*
"Polyethylene Glycol 400" (https://www.drugs.com/inactive/polyethylene-glycol-400-272.html)—access Sep. 1, 2021.*
Reintjes, T. (Ed.), "Solubility Enhancement with BASF Pharma Polymers: Solubilizer Compendium," Oct. 2011, BASF: The Chemical Company, Lampertheim, Germany, pp. 1-128.
Wu, X., et al., "Self-microemulsifying drug delivery system improves curcumin dissolution and bioavailability," *Drug Development and Industrial Pharmacy*, 2011, pp. 15-23, vol. 37(1).
Zhao, Y., et al., "Preparation of a bis-demethoxy curcumin microemuision based on pseudoternary phase diagrams and an orthogonal test analysis," *J. Pestic. Sci.*, 2011, pp. 248-251, vol. 36(2).
International Search Report (Form PCT/ISA/210) for International Application No. PCT/EP2013/065661, International Search Completed on Oct. 9, 2013, Applicant: Uwe-Bernd Rose.
Written Opinion of the International Searching Authority (Form PCT/ISA/237) for International Application No. PCT/EP2013/065661, Opinion Completed on Apr. 22, 2015, Applicant: Uwe-Bernd Rose.
"EF24—Calbiochem", Merck Millipore Website, [online] [Retrieved from the Internet Aug. 29, 2017: <URL: http://www.merckmillipore.com/DE/de/product/EF24—Calbiochem>. (2017) 2 pages.
"Derivate", Thieme ROMPP Online Dictionary, [online] [Retrieved from the Internet Aug. 29, 2017: <URL: https://roempp.thieme.de/roempp4.0/do/data/RD-04-00600 >. (Nov. 2005) 2 pages.
Mosley, C.A., et al., "Highly Active Anticancer Curcumin Analogues," The Molecular Targets and Therapeutic Uses of Curcumin in Health and Disease, 595: 77-103 (2007).

* cited by examiner

*Primary Examiner* — Susan Hoffman
(74) *Attorney, Agent, or Firm* — Alston & Bird LLP

(57) ABSTRACT

The subject matter of the invention is a pharmaceutical formulation which, according to the invention, contains curcumin or a curcumin derivative dissolved in an alcohol, an acid and an solubiliser. The formulation contains at most 12 percent by weight water and makes possible the production of an aqueous infusion solution, by means of which curcumin can be administered intravenously in dissolved form.

17 Claims, No Drawings

PHARMACEUTICAL COMPOSITION CONTAINING CURCUMIN

CROSS-REFERENCE TO RELATED APPLICATION

This application is a U.S. National Stage Application based on International Application No. PCT/EP2013/065661, filed Jul. 24, 2013, which designates the U.S. and was published by the International Bureau on Jan. 5, 2014, and which claims the benefit of German Patent Application No. DE 10 2012 219 219.0, filed Oct. 22, 2012, all of which are hereby incorporated by reference in their entirety.

FIELD OF THE INVENTION

The invention relates to a pharmaceutical formulation comprising curcumin or a curcumin derivative as active substance.

BACKGROUND OF THE INVENTION

Curcumin can be extracted from natural sources (for example, Javanese turmeric) or produced synthetically. Curcumin has antineoplastic properties, although no blood levels required for a systemic effect can be achieved, because curcumin is insoluble in water.

SUMMARY OF THE INVENTION

The task of the present invention is to create a pharmaceutical formulation of the genre mentioned above, which provides curcumin in a form that is sufficiently stable for storage and allows a simple and safe intravenous administration.

The subject matter of the invention is a pharmaceutical formulation comprising curcumin and/or a curcumin derivative, dissolved in an alcohol as well as additionally an acid and a solubilizer. The formulation according to the invention contains at most 12% by weight of water.

DETAILED DESCRIPTION OF THE INVENTION

First, we would like to explain a few terms used within the scope of the invention. A pharmaceutical formulation is a composition, which can be used either directly as end product for pharmaceutical purposes or can be transformed as intermediate product (preferably a storable intermediate product) in a simple fashion in a clinical environment by medical personnel into a ready-to-use form. Consequently, it only comprises pharmaceutically acceptable components.

Within the scope of the invention, the term curcumin derivative means natural and synthetic curcumin derivatives. Examples include naturally occurring curcuminoids. These are plant secondary metabolites that occur in the rootstocks of different *curcuma* plants such as e.g. turmeric [*curcuma Tonga*]. The term curcuminoids covers the three substances curcumin, demethoxycurcumin and bisdemethoxycurcumin. From a chemical point of view, curcuminoids are conjugated diarylheptanoids, i.e., polyphenols in the broader sense.

TABLE 1

Physical and chemical properties of curcuminoids [Govindarajan, 1980; Pedersen et al., 1985; Tønnesen et al., 1995].

| Trivial name | CUR | Demethoxy-CUR | Bisdemethoxy-CUR |
| --- | --- | --- | --- |
| Chemical name | Diferuloylmethane | 4-Hydroxycinnamoyl feruloyl methane | Bis-4-hydroxycinnamoyl methane |
| Total formula | $C_{21}H_{20}O_6$ | $C_{20}H_{18}O_5$ | $C_{19}H_{16}O_4$ |
| Molecular weight (g/mol) | 368.39 | 338.36 | 308.33 |
| Appearance | Yellow, crystalline powder | Orange-yellow, amorphous product | Yellow slabs |
| Melting point (° C.) | 182-183 | 172-174 | 223-224 |
| Max. absorption (EtOH) | 427 | 424 | 418 |
| Solubility | Insoluble in water, hexane, ether; soluble in alcohol, acetone, glacial acetic acid, organic solvents | | |

Furthermore, synthetically modified molecules can be produced, which have identical or similar physical and chemical properties, but can be physiologically more active. One example is EF-24:

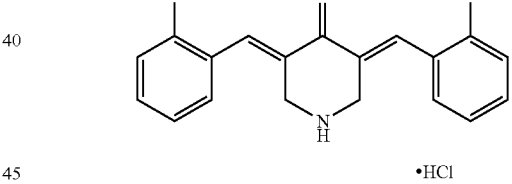

•HCl

EF-24 is an IKK inhibitor and synthetic curcumin analog. EF-24 is more potent than curcumin and has a considerably higher bioavailability; in addition, its potency in inducing cell death is 10 times greater. It has been shown to be more effective than Cisplatin in anti-tumor screening, and has a significantly lower potential of inducing adverse effects.

According to the invention, the curcumin derivatives are therefore preferably selected from the group comprising demethoxycurcumin, bisdemethoxycurcumin and synthetic curcumin analogs, in particular EF-24.

Curcumin is available in various tautomeric forms; a keto-enol tautomerism exists between a keto form and two equivalent enol forms. The keto-enol structure represents the unstable position of the curcumin molecule.

The chemical stability of curcumin in aqueous solutions is pH dependent. Under neutral to basic conditions, curcumin in aqueous solution is not stable. In alkaline solution, the dissociation of the enol takes place first (pKa 7.8), as a result of which the negative charge above the aromatic compounds is stabilized and the conjugated diene structure is destroyed.

The successive dissociation of the phenols subsequently follows in the alkaline environment (pKa 8.5 and 9.0).

Since the hydroxyl groups are present in undissociated form when the pH is acidic, the curcuminoids' stability is greater in this environment. The invention has recognized that curcumin does not disintegrate because of the higher physiological pH when it enters the blood stream, but binds to plasma protein and thus remains in the blood circulation. One attempt at explaining this phenomenon, which does not commit the applicant and limit the scope of protection, is that curcumin represents a lipophilic and polyphenolic compound and is therefore capable of interacting with macromolecules.

The formulation according to the invention preferably contains at most 5% by weight, more preferably at most 3% by weight of water, and more preferably it is free from water. Free from water means that no water is added or at the very most is added in such quantities that the keto-enol balance described above is not impaired.

The invention provides curcumin or a curcumin derivative as a storable and relatively concentrated solution; a solution for infusion can be produced in a simple fashion and in a clinical environment using the formulation according to the invention, in which curcumin can be dissolved in an aqueous environment and can therefore easily be administered intravenously. The invention has realized that curcumin can be brought into a relatively concentrated alcoholic solution, which allows the stable storage; according to the invention, the shelf life of said concentrate can be 2 years or longer.

A physiologically acceptable pH is achieved in the aqueous environment because of the acid present in the alcoholic concentrate when a solution for infusion is produced with the formulation according to the invention. The resulting solution for infusion preferably has a pH in the range of a weak acid. For example, the addition of citric acid to the concentrate achieves a pH from 5.5 to 6.0 in the aqueous solution for infusion, which remains stable for the entire duration of the infusion. The solubilizer according to the invention helps to ensure that curcumin remains in solution and does not precipitate in the aqueous environment after an aqueous solution for infusion has been prepared using the pharmaceutical formulation.

Ethanol is the particularly preferable type of alcohol used as solvent. The alcohol content preferably amounts to 40 to 90% by weight, more preferably to 40 to 70% by weight.

Inorganic acids such as e.g. phosphoric acid or hydrochloric acid can in principle be considered as acids. Organic acids are preferable. Suitable organic acids should preferably be provided in pure crystalline form, advantageously however at least in anhydrous form. Preferably, they should be soluble by at least 1% by weight in the used alcohol. The acid anion may not be a toxic substance, because it must be tolerable when administered intravenously. Preferable organic acids are tartaric acid, succinic acid, ethanoic acid, particularly preferably citric acid and ascorbic acid.

Ascorbic acid slows the degradation of curcumin in aqueous medium and thus also stabilizes an aqueous solution for infusion produced with the concentrate according to the invention. Ascorbic acid is physiologically active and is also used therapeutically as solution for infusion.

The solubilizers are preferably selected from the group of surface active substances (tensides or surfactants) and solubilizing polymers. Polyvinylpyrrolidones, ethylene oxide adducts of castor oil, polyethylene glycols and polysorbates are particularly preferable among the solubilizing polymers. Suitable solubilizers can be obtained for example from the company BASF and are described in the brochure entitled "Solubility Enhancement with BASF Pharma Polymers" (Solubilizer Compendium, October 2011, editor: Thomas Reintjes).

A suitable ethylene oxide adduct of castor oil can be obtained for example from BASF under the name Kolliphor ELP.

As an example, Polysorbate 80 (also known as Tween 80) is suitable among the polysorbates.

The pharmaceutical formulation according to the invention can preferably contain 0.2 to 3% by weight, preferably 0.5 to 2% by weight, more preferably 0.5 to 1.5% by weight of curcumin or curcumin derivative. The citric acid content (if applicable) preferably amounts to 0.2 to 1% by weight, more preferably to 0.3 to 0.5% by weight. The ascorbic acid content (if applicable) preferably amounts to 0.05 to 0.4% by weight, preferably to 0.07 to 0.15% by weight.

According to the invention, the ratio of citric acid (if applicable) to curcumin or curcumin derivative preferably amounts to 10 to 100 parts by weight, preferably to 15 to 50 parts by weight of citric acid per 100 parts by weight of curcumin or curcumin derivative. If ascorbic acid is added, 3 to 30 parts by weight, preferably 4 to 20 parts by weight of ascorbic acid are used per 100 parts by weight of curcumin or curcumin derivative.

The weight ratio of alcohol to solubilizer preferably amounts to 2:1 to 1:4, more preferably to 1:1 to 1:3.

Moreover, the subject matter of the invention is a method for the manufacture of a pharmaceutical formulation according to the invention. The method comprises the following steps:
  a. dissolution of the curcumin or curcumin derivative in alcohol,
  b. addition of the acid,
  c. mixing of the solubilizer with alcohol,
  d. mixing of the components obtained in b) and c).

A curcumin solution in alcohol (preferably ethanol) is produced first; in so doing, heating it up can be preferable (for example, to about 70° C.) to accelerate the dissolution process. The acid can already be present in the alcohol in dissolved form or it can be dissolved in the warm alcoholic curcumin solution.

A single-phase mixture of the solubilizer with alcohol is produced in a further step; said solution produced in step c) is added to the curcumin solution until the desired volume of the pharmaceutical formulation is obtained.

A solution for infusion comprising a carrier solution and a pharmaceutical formulation according to the invention dissolved in said carrier solution is another subject matter of the invention. According to the invention, the carrier solution can in particular be isotonic saline solution, glucose solution (for example 5% aqueous glucose solution) or another solution acceptable for infusion purposes.

The solution for infusion according to the invention is a single-phase solution, in which curcumin or the curcumin derivative is present in dissolved form. The solubilizers contained in the pharmaceutical formulation according to the invention help ensure that the curcumin or the curcumin derivative does not precipitate but remains in solution when the solution for infusion according to the invention is produced with the pharmaceutical formulation according to the invention and the carrier solution. The acid contained in the pharmaceutical formulation sets the desired physiological pH in the aqueous environment of the solution for infusion.

When an isotonic saline solution is used as carrier solution, a citric acid/citrate buffer develops in the solution for infusion according to the infusion, which sets and buffers the desired pH value (preferably 5 to 7, more preferably 5.5 to 6.5).

A solution for infusion according to the invention can preferably contain up to 0.2 to 4 mg, more preferably 0.5 to 1 mg of curcumin or curcumin derivative per mL of solution for infusion.

For example, 500 mL of solution for infusion can comprise between 250 and 450 mg of curcumin within the scope of the invention. A curcumin quantity required for a systemic therapy can be administered with the intravenous administration of the solution for infusion over a period of, for example, 90 min.

Furthermore, the object of the invention is a pharmaceutical formulation according to the invention or a solution for infusion to be used as a medicinal product, in particular an antineoplastic drug.

Exemplary embodiments of the invention are described below.

EXAMPLE 1

100 mg of curcumin are dissolved in 3.8 mL of absolute ethanol while stirring and heating to approximately 70° C. A clear, dark yellow solution has formed after 15 min.

40.7 mg of citric acid are dissolved without water in this solution.

25.88 g of Kalliphor ELP are mixed with 12.37 g of absolute ethanol. The mixture produced in this fashion is used to top up the previously produced curcumin solution to 10 mL.

The obtained solution is sterile filtered and autoclaved at 121° C.

A storable pharmaceutical formulation comprising curcumin in dissolved form is obtained in this fashion.

EXAMPLE 2

To produce a solution for infusion, the pharmaceutical formulation according to example 1 is poured into a carrier solution (preferably isotonic saline solution or 5% glucose solution), such that a curcumin concentration of 0.5 to 1 mg/mL is achieved in said solution for infusion.

EXAMPLE 3

An alcohol with a proportion of water is used as solvent in this example.

100 mg of curcumin are dissolved in 3.8 mL of 70% ethanol (the remainder is water) while stirring and heating to approximately 70° C. A clear, dark yellow solution has formed after 15 min.

10 mg of ascorbic acid are dissolved without water in said solution.

25.88 g of Kalliphor ELP are mixed with 12.37 g of absolute ethanol. The mixture produced in this fashion is used to top up the previously produced curcumin solution to 10 mL.

The obtained solution is sterile filtered and autoclaved at 121° C.

A storable pharmaceutical formulation comprising curcumin in dissolved form is obtained in this fashion. The proportion of water is approximately 12% by weight.

A higher curcumin concentration is dissolved in the pharmaceutical formulation in examples 4 and 5 below.

EXAMPLE 4

150 mg of curcumin are dissolved in 4 mL of absolute ethanol while stirring and heating to approximately 70° C. A clear, dark yellow solution has formed after 15 min.

34 mg of citric acid are dissolved without water in said solution.

25.88 g of Kalliphor ELP are mixed with 12.37 g of absolute ethanol. The mixture produced in this fashion is used to top up the previously produced curcumin solution to 10 mL.

The obtained solution is sterile filtered and autoclaved at 121° C.

A storable pharmaceutical formulation comprising curcumin in dissolved form is obtained in this fashion.

EXAMPLE 5

150 mg of curcumin are dissolved in 4 mL of absolute ethanol while stirring and heating to approximately 70° C. A clear, dark yellow solution has formed after 15 min.

10 mg of ascorbic acid are dissolved without water in said solution. 25.88 g of Kalliphor ELP are mixed with 12.37 g of absolute ethanol. The mixture produced in this fashion is used to top up the previously produced curcumin solution to 10 mL.

The obtained solution is sterile filtered and autoclaved at 121° C.

A storable pharmaceutical formulation comprising curcumin in dissolved form is obtained in this fashion.

That which is claimed:

1. A pharmaceutical formulation for intravenous administration, characterized in that it comprises curcumin and/or a curcumin derivative, an alcohol, an acid, and a solubilizer; wherein the curcumin and/or the curcumin derivative is dissolved in the alcohol; and wherein no water has been added to the formulation, or wherein water has been added in a quantity that does not impair the curcumin and/or curcumin derivative's keto/enol balance; and wherein the solubilizer is selected from the group consisting of polyvinylpyrrolidones, ethylene oxide adducts of castor oil and polysorbates.

2. A pharmaceutical formulation according to claim 1, characterized in that the curcumin derivative is selected from the group consisting of demethoxycurcumin, bisdemethoxycurcumin and synthetic curcumin analogs.

3. A pharmaceutical formulation according to claim 1, characterized in that the alcohol is ethanol.

4. A pharmaceutical formulation according to claim 1, characterized in that the alcohol content is 40 to 90% by weight.

5. A pharmaceutical formulation according to claim 1, characterized in that the acid is ascorbic acid or a food acid.

6. A pharmaceutical formulation according to claim 1, characterized in that it comprises 0.2 to 3% by weight of curcumin or curcumin derivative.

7. A pharmaceutical formulation according to claim 1, characterized in that it comprises 0.2 to 1% by weight of citric acid.

8. A pharmaceutical formulation according to claim 1, characterized in that it comprises 0.05 to 0.4% by weight of ascorbic acid.

9. A pharmaceutical formulation according to claim 1, characterized in that it comprises 10 to 100 parts by weight of citric acid per 100 parts by weight of curcumin or curcumin derivative.

10. A pharmaceutical formulation according to claim 1, characterized in that it comprises 3 to 30 parts by weight of ascorbic acid per 100 parts by weight of curcumin or curcumin derivative.

11. A pharmaceutical formulation according to claim 1, characterized in that the weight ratio of alcohol to solubilizer is 2:1 to 1:4.

12. A method for the manufacture of a pharmaceutical formulation according to claim 1, characterized by the following steps:
 a) Dissolution of the curcumin or curcumin derivative in alcohol,
 b) Addition of the acid,
 c) Mixing of the solubilizer with alcohol,
 d) Mixing of the components obtained in b) and c).

13. A solution for infusion, characterized in that it comprises a carrier solution and a pharmaceutical formulation according to claim 1 dissolved in said carrier solution.

14. A solution for infusion according to claim 13, characterized in that the carrier solution is selected from the group of isotonic saline solution and glucose solution.

15. A solution for infusion according to claim 13, characterized in that it comprises 0.2 to 4 mg/mL of curcumin or curcumin derivative.

16. A pharmaceutical formulation according to claim 1 for use as medicinal product.

17. A solution for infusion according to claim 13 for use as medicinal product.

\* \* \* \* \*